(12) United States Patent
Mendonca et al.

(10) Patent No.: US 8,208,707 B2
(45) Date of Patent: Jun. 26, 2012

(54) TISSUE CLASSIFICATION IN MEDICAL IMAGES

(75) Inventors: Paulo Ricardo Mendonca, Clifton Park, NY (US); Saad Sirohey, Pewaukee, WI (US); Rahul Bhotika, Albany, NY (US); Fei Zhao, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 964 days.

(21) Appl. No.: 12/202,912

(22) Filed: Sep. 2, 2008

(65) Prior Publication Data
US 2010/0054563 A1    Mar. 4, 2010

(51) Int. Cl.
*G06K 9/00* (2006.01)

(52) U.S. Cl. ..................... 382/131; 382/128

(58) Field of Classification Search .......... 382/128, 382/131
See application file for complete search history.

(56) References Cited

U.S. PATENT DOCUMENTS

| 6,947,784 B2 | 9/2005 | Zalis | |
| 2003/0223627 A1* | 12/2003 | Yoshida et al. | 382/128 |
| 2009/0022375 A1* | 1/2009 | Fidrich et al. | 382/128 |

OTHER PUBLICATIONS

Summers, Ronald M., et al.; Technical Innovation: "Computer-Aided Detection of Polyps on Oral Contrast-Enhanced CT Colonography'" AJR:184, Jan. 2005.

Mendonca, Paulo R.S.; "Lung Nodule Detection via Bayesian Voxel Labeling," IPMI 2007, LNCS 4584; pp. 134-146.

Melonakos, John; "A Probabilistic Model for Haustral Curvatures with Applications to Colon CAD," MICCAI 2007, Part II, LNCS 4792, pp. 420-427.

Mendonca, Paulo R.S.; "Detection of Polyps via Shape and Appearance Modeling," Proc MICCAI 2008 Workshop: Computational and Visualization Challenges in the New Era of Virtual Colonoscopy, pp. 33-39.

* cited by examiner

*Primary Examiner* — Clayton E Laballe
*Assistant Examiner* — Noam Reisner
(74) *Attorney, Agent, or Firm* — Scott J. Asmus

(57) ABSTRACT

The present disclosure relates to the use of probabilistic models to classify elements of a medical image into different tissue types. The models may be based upon geometric abstractions of the different tissue types being classified. In addition, the present disclosure teaches the derivation and modification of models for tissue classification based upon the neighboring region of the voxels undergoing classification.

20 Claims, 3 Drawing Sheets

TISSUE CLASSIFICATION IN MEDICAL IMAGES

BACKGROUND

The invention relates generally to medical imaging and, in particular, to the identification of different anatomical and/or pathological structures in medical images.

Non-invasive medical imaging technologies allow a caregiver to obtain and view images of the internal structures and organs of a patient without performing surgery or other invasive procedures. In particular, technologies such as X-ray radiography, computed tomography (CT), tomosynthesis, magnetic resonance imaging (MRI), ultrasound, C-arm angiography, positron emission tomography (PET), and single positron emission computed tomography (SPECT) use various physical principles to create two-dimensional and/or three-dimensional representations of the interior of the human body. For example, in those imaging modalities utilizing X-rays, the principle of operation typically involves assessing the differing attenuation of the X-rays by the patient's body at one or more angles. Based upon the differential attenuation attributable to different tissues, a two- or three-dimensional image may be reconstructed that accurately depicts the internal structure of the patient. Different imaging modalities apply differing physical principles, but in each case a useful image derived using some property of the patient's body is produced.

To utilize some of the imaging modalities or to image certain anatomic regions, a patient may be treated prior to imaging to improve the image quality. For example, as part of the process of acquiring CT images of the colon, the patient may undergo catharsis, or colon cleansing, to cause the expulsion of the contents of the colon. In addition, the colon may be inflated or pressurized with air. These processes are very uncomfortable to the patient and may result in the patient not complying with the periodic screening schedule recommended for the patient. As a result, the patient may not be screened as frequently as recommended. Likewise, the imaging protocols for other organs may be similarly uncomfortable and may discourage or prevent patient compliance with the appropriate examination schedule. Therefore, it may be desirable to reduce or eliminate the uncomfortable preliminary steps involved in imaging various organs.

BRIEF DESCRIPTION

The present disclosure relates to the derivation and application of different probabilistic models to classify voxels of an image into different tissue types, such as healthy structures (colonic folds, blood vessels, and so forth) and abnormal structures (sessile polyps, pedunculated polyps, nodules, and so forth). In certain embodiments, contrast-agents may be employed so that enhanced regions of the image, such as the fluid and/or solid contents of an organ, may be easily distinguished. In such embodiments, the enhanced region is not subtracted from the image during subsequent analysis but is instead employed to select the appropriate models for analyzing the various tissue voxels in the image. For example, different models may be employed to evaluate those tissue voxels near the contrast-enhanced region and those tissue voxels near a region of air within the organ.

In one embodiment, a method is provided. The method includes the act of generating an initial region mask of a volumetric representation of an organ. A plurality of voxels to be labeled are defined based upon the initial region mask. Models used to label the voxels are adjusted based on neighboring regions of a respective voxel undergoing labeling. Each voxel of the plurality of voxels is labeled as corresponding to one of a tissue type, an anatomical structure, or organ contents based using the respective adjusted models.

In a further embodiment, a method is provided. The method includes the act of computing one or more respective features for each tissue voxel of a plurality of tissue voxels. A respective gradient is calculated for each tissue voxel of the plurality of tissue voxels. Each tissue voxel is labeled based upon the respective features and the gradient and the proximity of the respective tissue voxel to adjacent structures or contents of an organ.

In another embodiment, a method if provided. The method includes the act of acquiring volumetric image data of an organ using a computed tomography scanner. The volumetric image data is processed to identify a plurality of tissue voxels in the volumetric image data. The plurality of tissue voxels is processed using two or more models. The proximity of each tissue voxel to different adjacent regions, organ contents or anatomical structures is used to adjust the two or more models.

In an additional embodiment, an image processing system is provided. The image processing system includes one or more storage devices storing one or more image processing routines. The stored routines include a routine configured to generate an initial region mask of a volumetric representation of an organ, a routine configured to define a plurality of voxels to be labeled based upon the initial region mask, a routine configured to adjust models used to label the voxels based on neighboring regions of a respective voxel undergoing labeling, and a routine configured to label each voxel of the plurality of voxels as corresponding to one of a tissue type, an anatomical structure, or organ contents based using the respective adjusted models. The image processing system also includes a processor configured to execute the one or more image processing routines.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present techniques are directed to the identification of different anatomical and/or pathological structures in medical images. The technique may be useful for distinguishing between certain types of tissues in different organs. For example, the present disclosure may be useful in distinguishing between lung nodules and healthy lung tissue. Likewise, the techniques may be useful for distinguishing between colon polyps and healthy colon tissue or for identifying other tissue types associated with other organs. In one embodiment, shape-based descriptors are used classify elements of an image (such as voxels in a three-dimensional representation) as different tissue types of interest. In this manner, different structural elements within an image may be labeled in accordance with the type of tissue they represent.

Figure 1:
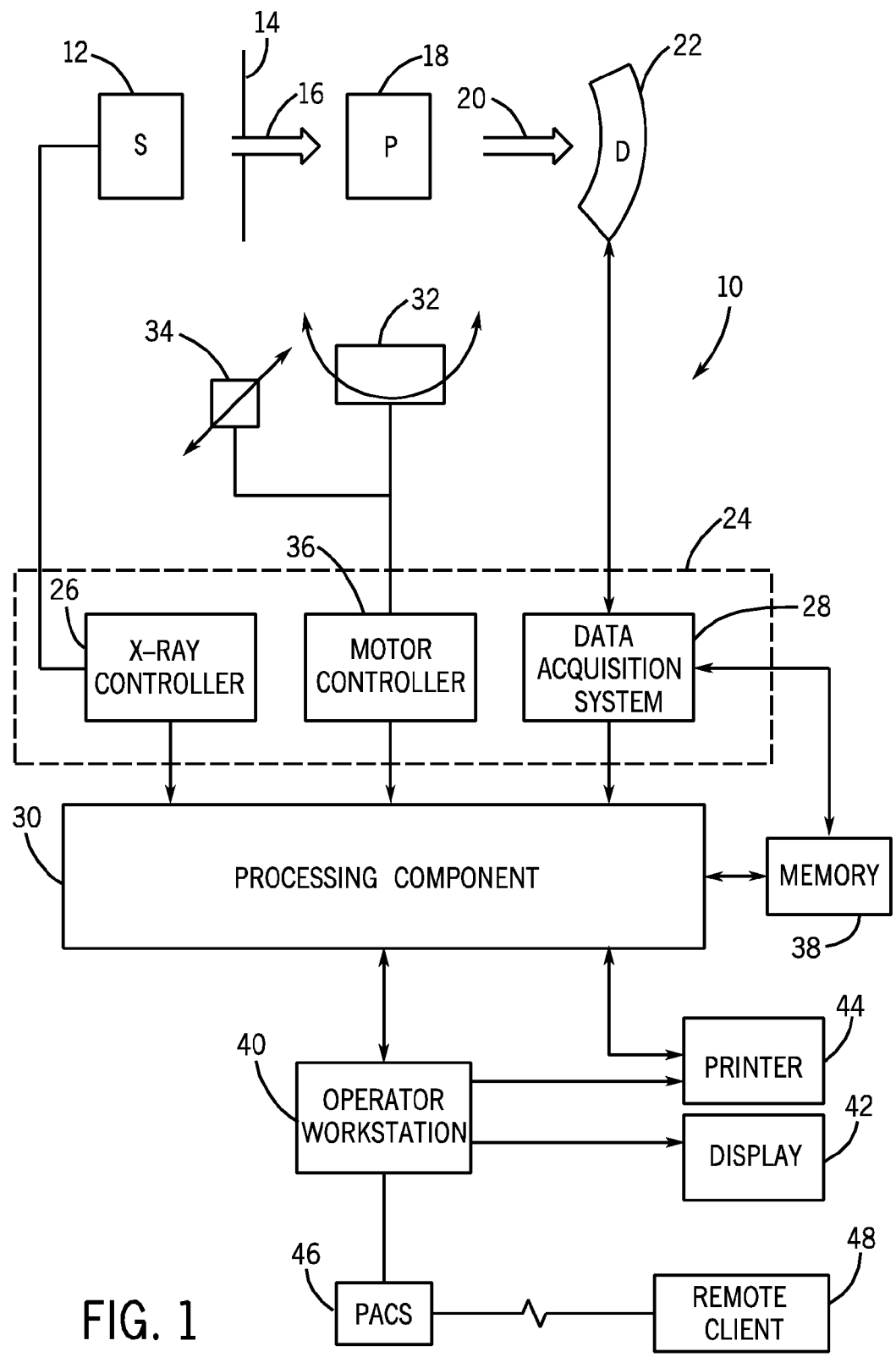
FIG. 1 is a diagrammatical view of an exemplary imaging system in the form of a CT imaging system for use in producing images in accordance with one embodiment of the present technique.

With this in mind, an example of a computer tomography (CT) imaging system that may be used to acquire images processed in accordance with the present techniques is provided in FIG. 1. Though a CT system is described by way of example, it should be understood that the present techniques may also be useful when applied to images acquired using other imaging modalities, such as tomosynthesis, MRI, PET, SPECT, C-arm angiography, mammography ultrasound, and so forth. The present discussion of a CT imaging modality is provided merely as an example of one suitable imaging modality.

Turning now to FIG. 1, this figure illustrates an imaging system 10 for acquiring and processing projection data to produce reconstructed images that may be processed in accordance with the present techniques. In one embodiment, system 10 is a CT system designed to acquire X-ray attenuation data at a variety of views around the patient. In the embodiment illustrated in FIG. 1, imaging system 10 includes a source of X-ray radiation 12 positioned adjacent to a collimator 14. The X-ray source 12 may be an X-ray tube, a distributed X-ray source (such as a solid-state or thermionic X-ray source) or any other source of X-ray radiation suitable for the acquisition of medical images.

The collimator 14 permits X-rays 16 to pass into a region in which a patient 18, is positioned. A portion of the X-ray radiation 20 passes through or around the patient 18 and impacts a detector array, represented generally at reference numeral 22. Detector elements of the array produce electrical signals that represent the intensity of the incident X-rays 20. These signals are acquired and processed to reconstruct images of the features within the patient 18.

Source 12 is controlled by a system controller 24, which furnishes both power, and control signals for CT examination sequences. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which controls acquisition of the signals generated in the detector 22. In the depicted embodiment, the system controller 24 acquires the signals generated by the detector using a data acquisition system 28. The data acquisition system 28 receives data collected by readout electronics of the detector 22. The data acquisition system 28 may receive sampled analog signals from the detector 22 and convert the data to digital signals for subsequent processing by a processor 30 discussed below. Alternatively, in other embodiments the digital-to-analog conversion may be performed by circuitry provided on the detector 22 itself. The system controller 24 may also execute various signal processing and filtration functions with regard to the acquired image signals, such as for initial adjustment of dynamic ranges, interleaving of digital image data, and so forth.

In the embodiment illustrated in FIG. 1, system controller 24 is coupled to a rotational subsystem 32 and a linear positioning subsystem 34. The rotational subsystem 32 enables the X-ray source 12, collimator 14 and the detector 22 to be rotated one or multiple turns around the patient 18. It should be noted that the rotational subsystem 32 might include a gantry upon which the respective X-ray emission and detection components are disposed. Thus, in such an embodiment, the system controller 24 may be utilized to operate the gantry.

The linear positioning subsystem 34 may enable the patient 18, or more specifically a table supporting the patient, to be displaced within the bore of the CT system 10. Thus, the table may be linearly moved within the gantry to generate images of particular areas of the patient 18. In the depicted embodiment, the system controller 24 controls the movement of the rotational subsystem 32 and/or the linear positioning subsystem 34 via a motor controller 36.

In general, system controller 24 commands operation of the imaging system 10 (such as via the operation of the source 12, detector 22, and positioning systems described above) to execute examination protocols and to process acquired data. For example, the system controller 24, via the systems and controllers noted above, may rotate a gantry supporting the source 12 and detector 22 about a subject of interest so that a plurality of radiographic views may be collected for processing. In the present context, system controller 24 may also includes signal processing circuitry, associated memory circuitry for storing programs and routines executed by the computer (such as routines for executing image processing techniques described herein), as well as configuration parameters, image data, and so forth.

In the depicted embodiment, the image signals acquired and processed by the system controller 24 are provided to a processing component 30 for reconstruction of images. The processing component 30 may be one or more conventional microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid state memory storage structures. Moreover, the memory 38 may be located at the acquisition system site and/or may include remote storage devices for storing data, processing parameters, and/or routines for iterative image reconstruction described below.

The processing component 30 may be configured to receive commands and scanning parameters from an operator via an operator workstation 40, typically equipped with a keyboard and/or other input devices. An operator may control the system 10 via the operator workstation 40. Thus, the operator may observe the reconstructed images and/or otherwise operate the system 10 using the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the imaging system 10 separately, these various components may be provided within a common platform or in interconnected platforms. For example, the processing component 30, memory 38, and operator workstation 40 may be provided collectively as a general or special purpose computer or workstation configured to operate in accordance with the present technique. In such embodiments, the general or special purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition.

Figure 2:
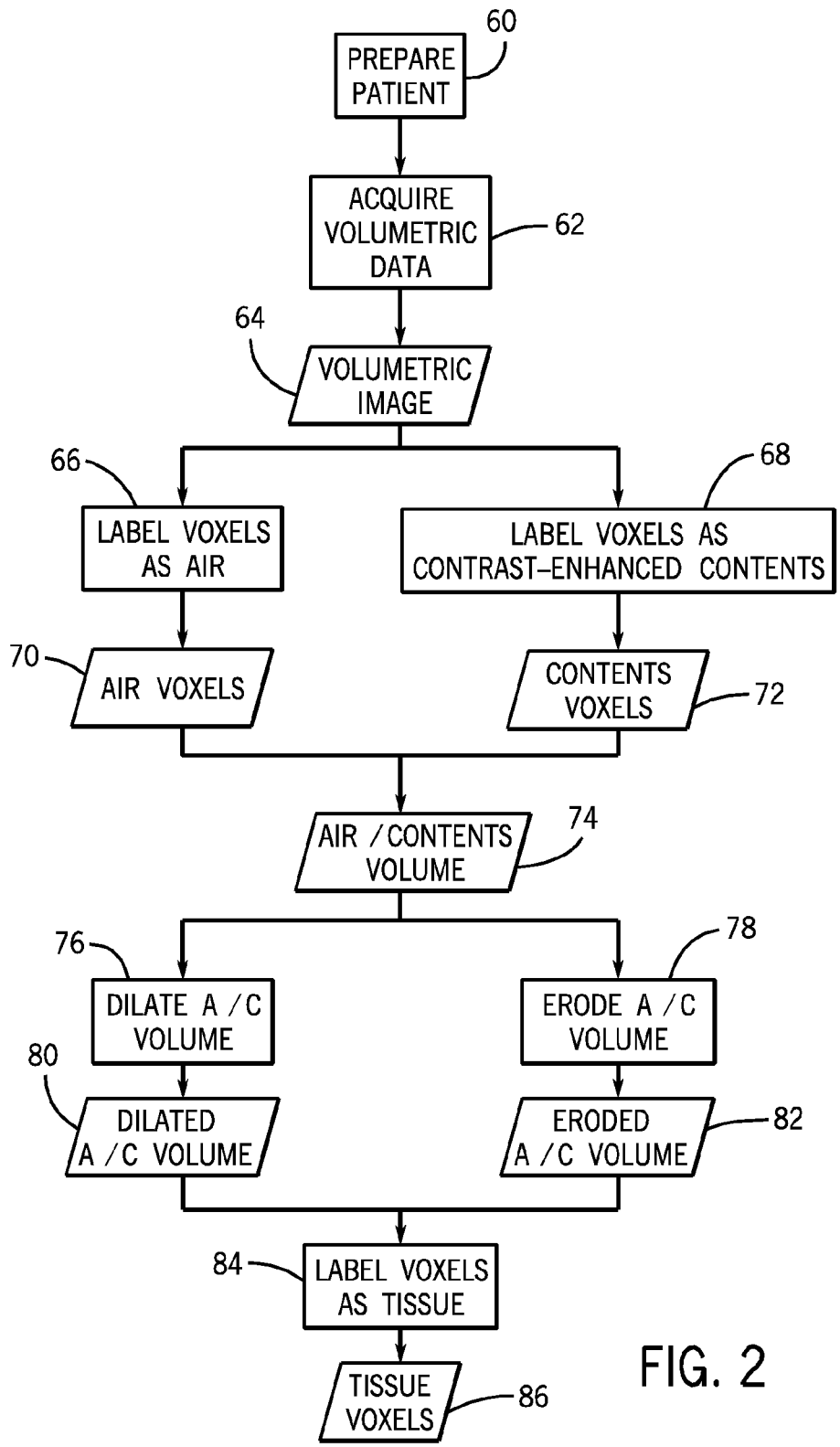
FIG. 2 is a flowchart depicting various stages in the identification of tissue voxels, in accordance with one embodiment of the present technique.

With the foregoing example of one suitable image acquisition system in mind, a technique for processing images acquired using such a system is now discussed. For example, in one embodiment, the system 10 discussed above is used to acquire and/or process three-dimensional images of a patient's colon, lungs, or other suitable organs. Turning now to FIG. 2, a flowchart depicting aspects of an algorithm used to identify those elements of a three-dimensional image that represent tissue are provided. In this embodiment, the patient 18 may be initially prepared (block 60) prior to imaging, such as by administration of one or more contrast agents.

For example, in a colon-imaging embodiment, a contrast agent, such as an iodine-based agent, may be administered to the patient 18 prior to acquisition (block 62) of three-dimensional (i.e., volumetric) image data 64, such as using the CT imaging system of FIG. 1. In one such embodiment, the patient 18 does not undergo catharsis, i.e., colon cleansing, and, therefore, the colon typically contains fluids and solids (i.e., contents) as well as air. The contrast agent mixes with the contents in the colon to increase the opacity of these contents to X-rays. In some such embodiments, the colon may also be inflated, i.e., injected with air. However, in these embodiments the colon still contains both air and the contrast-enhanced contents.

The volumetric image 64 thus obtained may be processed to label (blocks 66, 68) the voxels 70 representing air and the voxels 72 representing contrast-enhanced contents of the colon. In one embodiment, the voxels of the volumetric image 64 may be about 0.6 mm×0.6 mm×0.6 mm, though in other embodiments the voxels need not be cubic any may instead be about 0.6 mm×0.6 mm×1.0 mm or some other suitable size. In one embodiment, a voxel may be labeled as air or contents based on a comparison of the intensity of the voxel with respective threshold values. For example, air typically provides little or no attenuation of X-rays so a voxel representing a region consisting mostly of air will appear black or otherwise dark in a typical CT volume rendering. Thus, in one embodiment, those voxels having an intensity less than a given threshold may be labeled as air voxels 70. Conversely, contrast-enhanced contents of the colon will be highly attenuating to X-rays. Therefore, a voxel representing a region consisting mostly of contrast-enhanced contents will appear white or otherwise light in a typical CT volume rendering. Thus, in one embodiment, those voxels having an intensity greater than another given threshold may be labeled as contents voxels 72.

Because the colon is assumed to contain either air or contrast-enhanced contents at the time of imaging, an air/contents volume 74 representing the interior of the colon may be defined based on the respective air voxels 70 and contents voxels 72. The air/contents volume 74 may be used to identify the colon tissue in the volumetric image 64. For example, in one embodiment, the air/contents volume 74 is both dilated (block 76) and eroded (block 78) in accordance with known image processing techniques to generate both a dilated air/contents volume 80 and an eroded air/contents volume 82. In this manner, a dilated air/contents volume 80 that is slightly enlarged, i.e., includes additional voxel elements at the periphery, relative to the air/contents volume 74 is obtained. An eroded air/contents volume 82 that is slightly reduced relative to the air/contents volume 74 is also obtained.

Because the air/contents volume 74 defines the interior of the colon, the difference between the dilated air/contents volume 80 and the eroded air/contents volume 82 may be used to inclusively label voxels (block 84) as corresponding to the surface tissue 86 of the colon interior. That is, by using those voxels present in the difference image obtained by subtracting the eroded air/contents volume 82 from the dilated air/contents volume 80, voxels that are near or only partially representative of tissue may be classified as tissue for further processing purposes. In this way, those voxels that are ambiguous as to whether they primarily represent tissue, air, or contents of the colon may be classified as tissue voxels 86 such that no interface tissue voxels are misclassified. Thus, the volumetric image 64 may be processed such that the voxels are classified as corresponding to air, colon contents, or colon tissue.

Figure 3:
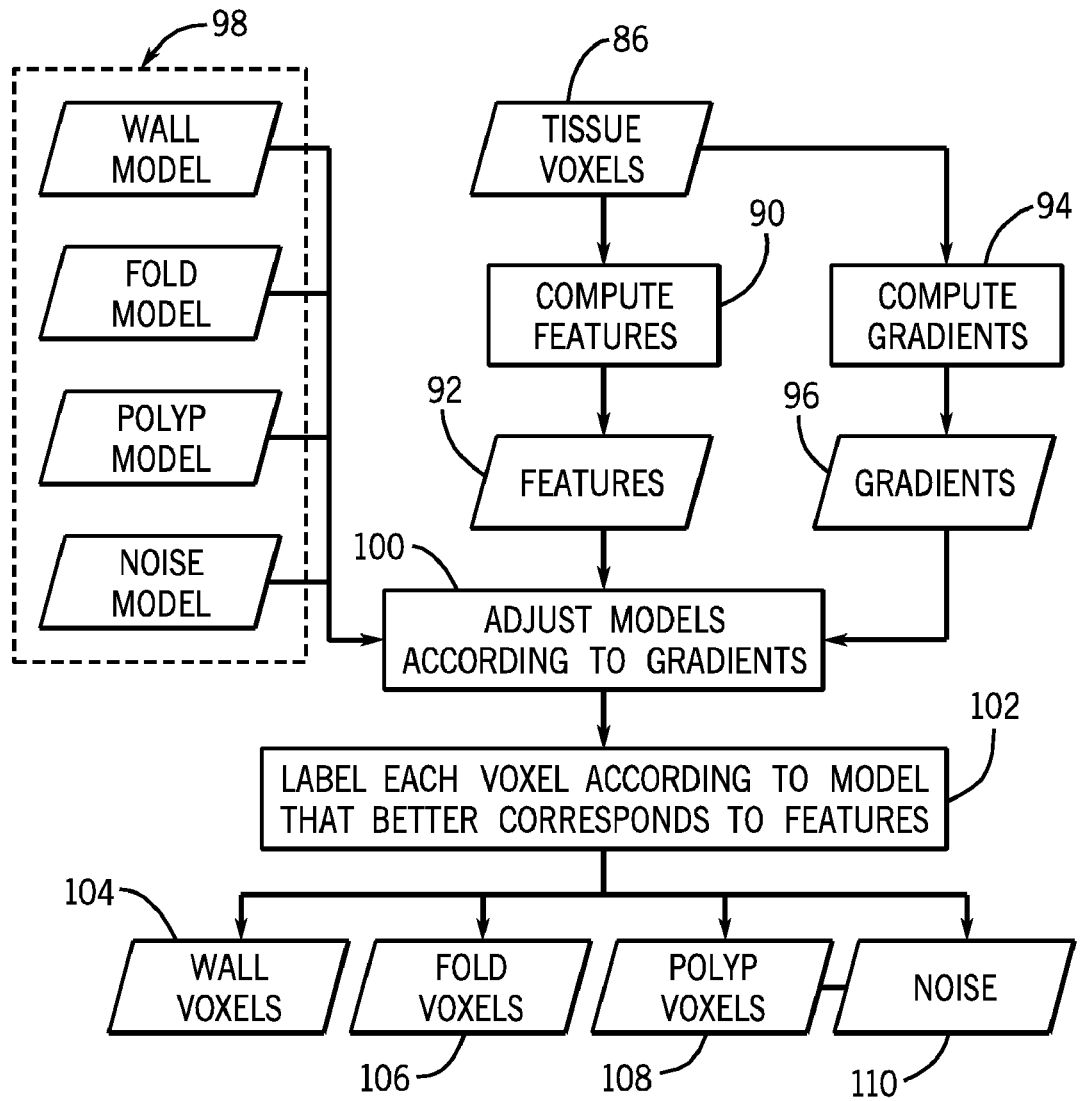
FIG. 3 is a flowchart depicting various stages in the classification of tissue voxels into different tissue types, in accordance with one embodiment of the present technique.

Turning now to FIG. 3, the tissue voxels 86 may be processed to further classify them as polyp tissue, healthy tissue, and/or noise. In particular, shape characteristics, such as curvature, of the voxels may be utilized to classify the tissue voxels 86. In one embodiment, this may be accomplished by calculating (block 90) features 92 in the neighborhood of each respective tissue voxel. The neighborhood of a respective voxel may be arbitrarily defined and, in one embodiment, may be a cube, such as a 5×5×5 or 7×7×7 voxel array defined about the respective voxel of interest. In other embodiments, the neighborhood may be defined by a segmentation algorithm such that the different boundaries identified by the segmentation algorithm form the boundaries of each neighborhood.

Further, a feature 92 may, in one embodiment, be construed to be any function of the intensity of a voxel within its neighborhood. Examples of such features 92 may include, but are not limited to, a curvature, an average intensity within a region, a variation of intensity within a region, a histogram of the intensity within a region, one or more gradients within the region, or other quantitative or qualitative descriptors that describe the voxel within its neighborhood. In accordance with one aspect of the present disclosure, the feature 92 is one which allows effective discrimination between different types of tissue and/or structures.

The features 92 may then be used, in conjunction with context information about whether the voxel is proximate to contrast-enhanced colon contents or air and the computed (block 94) gradients 96, to adjust (block 100) models 98 of the different anatomical and/or pathological structures of interest. The adjusted models 98 may then be used to label (block 102) each respective voxel as corresponding to healthy tissue (i.e., wall voxels 104 or fold voxels 106), polyp tissue (i.e., polyp voxels 108), or noise 110. For example, in certain embodiments discussed below, the gradient 96 and context information for each voxel may be input to a respective mathematical model for each category type. Each voxel is then categorized based on the respective model outputs for each respective voxel.

With the foregoing in mind, the following example is provided by way of illustration. In this example, a patient is administered a contrast agent, such as an iodine-based agent, that renders the contents of the patient's colon generally opaque to X-rays. In addition, air may be injected into the patient's colon prior to imaging. The prepared patient may be imaged using a CT system to obtain one or more three-dimensional, i.e., volumetric, representations of the colon.

A volumetric representation of the colon is then processed such that voxels having an intensity above a first threshold are labeled as contents voxels (corresponding to the fluid and solid colon contents) and voxels having an intensity below a second threshold are labeled as air voxels. As described herein, the combination of the air and contents voxels constitute an air/contents volume that may be both dilated (such as by the addition of one or more layers of voxels to the periphery) and eroded (such as by the removal of one or more layers of voxels from the periphery) to generate respective dilated and eroded volumes. Upon subtraction of the eroded volume from the dilated volume, the remaining voxels (i.e., the difference between the eroded and dilated volumes) may be labeled as tissue voxels.

The tissue voxels may be processed to compute gradients for each respective tissue voxel. In this example, each gradient is a vector indicating the largest positive direction of intensity change within the voxel, i.e., the vector points from the darkest point in the voxel to the brightest point in the voxel. Thus, voxels adjacent to the contrast-enhanced contents of the colon will generally have a gradient that points from the colon tissue toward the contents. Conversely, voxels adjacent to the air within the colon will generally have a gradient that points from the air within the colon toward the colon tissue.

In one embodiment, features computed in regions, such as neighboring regions, pertaining to each tissue voxel may be used to ascertain a discernible characteristic of the voxel, such as a shape characteristic, including measures of curvature or other geometric properties. The discernible characteristic may, in turn, be used to classify the voxel as representing a particular type of tissue. In one embodiment, this classification may be accomplished using one or more parametric models that evaluate one or more geometric characteristics associated with the voxel and the surrounding environment. The gradients of each tissue voxel may be used to control or adapt the parametric models in accordance with the surrounding environment, as described above.

For example, near the tissue interface with the air within the colon, tissue voxels that depict the colon wall may generally be expected to exhibit a slightly negative curvature in all tangent directions, i.e., to be slightly concave. Conversely, near the wall interface with the contrast-enhanced contents of the colon, tissue voxels that depict the colon wall may generally be expected to exhibit a slightly positive curvature in all tangent directions, i.e., to be slightly convex, due to the opposite intensity properties of contrast-enhanced contents and the air. Thus voxels demonstrating slight degrees of concavity (near the air environment) or convexity (near the environment of the contrast-enhanced contents) in at least one direction may be classified based on their shape as corresponding to the tissue of the colon wall.

Folds in the colon wall may have different geometric characteristics than other regions of the colon wall. For example, near the tissue interface with the air within the colon, tissue voxels that depict a fold in the colon wall may generally be expected to exhibit a high positive curvature in the direction along the fold, and low, either positive or negative, curvature in the direction across the fold. Conversely, near the tissue interface with the contrast-enhanced contents of the colon, tissue voxels that depict a fold in the colon wall may generally be expected to exhibit a high negative curvature in the direction along the fold and low, either negative or positive, curvature in the direction across the fold. Thus voxels demonstrating high degrees of inward curvature in a single direction (near the air environment) or outward curvature in a single direction (near the environment of the contrast-enhanced contents) and low curvature in another direction may be classified based on their shape as corresponding to folds in the tissue of the colon wall.

Conversely, polyps near the tissue interface with the air within the colon may generally be expected to exhibit a high positive curvature when viewed from any direction, i.e., to be convex. Conversely, polyps near the tissue interface with the contrast-enhanced contents of the colon may generally be expected to exhibit a high negative curvature when viewed from any direction, i.e., to be concave. Thus voxels demonstrating high degrees of convexity (near the air environment) or concavity (near the environment of the contrast-enhanced contents) in any direction may be classified based on their shape as corresponding to polyp tissue.

Thus, based on the expected shape characteristics of different types of tissue, each voxel may be modeled to determine if its shape corresponds to tissue wall, folds in the wall, or polyps. Based on the model results, each voxel may be labeled as one of these tissue types or as an outlier, i.e., noise, if no model proves satisfactory at describing the shape characteristics of a voxel. Likewise, to the extent that different types of polyps may have different shape characteristics, different models may be employed such that a voxel might be characterized not merely as corresponding to polyp tissue, but to a particular type of polyp tissue.

With the foregoing in mind, the following example is provided to illustrate one possible embodiment of the models used in classifying tissue voxels. In this embodiment, predictive stochastic models may be derived for the relevant shape features (such as the curvature features noted above) to be used in the tissue classification process. For example, using Bayes law and marginalizing over the model parameters, a probability that a voxel (x) is defined by a model (M) of a set of parametric models ($M_i$, i=1, ... N) that each mathematically describe a respective colorectal structure, may be given by:

$$P(M_i \mid D, x) = M' \times \frac{P(M_i \mid x)}{p(D \mid x)} \prod_{j=1}^{M} \int_{M_i} p(D_j \mid m_i, M_i, x) p(m_i \mid M_i, x) dm_i \qquad (1)$$

where each model $M_i$ has parameters $m_i$ in the domain $M_i$, and where given a choice of $M_i$, D is assumed to be a set of D={$D_j$, j=1, ... M} of independent datum $D_j$ associated with voxel x.

In an embodiment where curvature κ is the shape characteristic used to discriminate between colorectal structures:

$$D_j = \kappa(x_j) \qquad (2)$$

for $x_j \in B(x)$ where B(x) is a neighborhood of the voxel x. Laplace's method may be used to compute the integral in Equation 1 once $p(D_j \mid m_i, M_i, x)$ and $p(m_i \mid M_i, x)$ are available. In one embodiment, image voxels may then be labeled in accordance with the appropriate functions of $P(M_i \mid D, x)$ such that each voxel is labeled based on the greatest probability of correct classification. For example, in an embodiment where there are models defining the probability that a voxel is associated with colon tissue walls, folds, sessile polyps, pedunculated polyps, and/or noise, the model yielding the highest probability for a given voxel may be used to classify the respective voxel.

The probability $p(D_j|m_i,M_i,x)$ for each colorectal structure may be derived by analytically modeling the shape and/or appearance of each respective colorectal structure and then by sampling from the analytical models and mapping the sampled points on the model to curvature values using classical differential geometry or the geometry of Gaussian random fields. In this manner, a probability function may be derived for each analytical model describing the various shapes of the structures to be classified.

The modeling of the prior, $p(m_i|M_i,x)$ in Equation 1 may be based on domain knowledge of the anatomy and/or physiology in question, such as the anatomy and physiology of the colon or lung in certain embodiments. In embodiments where the amount of clinical data is less than desired to describe the probability density, it may be useful to set-up least informative priors given the available constraints as the maximum entropy principle. In such an embodiment, the maximum entropy principle prescribes for $p(m_i|M_i,x)$ the probability density that maximizes $S=-\int p(x)\log p(x)dx$ given integral constraints in the form $E[f_k(x)]=c_k$ where $E$ is the expectation functional. In such an embodiment, clinical knowledge may be incorporated in the functions $f_k$ and the parameters $c_k$, thereby mathematically encoding information such as expected values for the polyp diameter and/or the width of the colonic folds.

In addition, solving Equation 1 also utilizes two additional pieces of information. The first piece of information is $P(M_i|x)$, which may be obtained from anatomical and/or epidemiological information on a screening patient cohort. An example of anatomical and/or epidemiological information that may be obtained and used in this manner is polyp prevalence and/or size distribution. Once such an estimate is available, $P(M_i|x)$ may be computed as a relative volume ratio. For example, $P(M_i|x)$ may be given by the ratio of the expected volume of polyps per patient and the expected volume of all colonic structures.

With regard to the second piece of information, the distribution $p(\kappa|M_i,x)$ may be derived under the assumption that the voxel $x$ is sampled from model $M_i$. However, the datum $D_j$ in $p(D_j|M_i,x)$ may be extracted from a voxel $x_j$ that is not equal to $x$. This may be accounted for by assuming that the voxels of model $M_i$ are located in a spherical region $R$ of radius $S$, where $S$ can be estimated from $p(m_i|M_i,x)$. If $x$ is sampled from $R$ according to a Poisson point process, and a voxel $x_j$ is subsequently sampled among the set of all voxels at a distance $d$ from $x$, also according to a Poisson point process, the probability $\omega_{d,s}$ that $x_j$ belongs to $R$ can be computed as:

$$\omega_{d,s}=(d-2S)^2(d+4S)/16S^3 I_{S \geq d/2}(S) \quad (3)$$

which yields:

$$p(D_j|M_i,x)=\omega_{\|x_j-x\|,S} p(\kappa|M_i,x)+(1-\omega_{\|x_j-x\|,S})p(\kappa|M_4,x)$$
where there are four models under consideration. (4)

With the foregoing discussion in mind and by way of example, in an embodiment based on analysis of colon volumetric images colon polyps and folds may be modeled based on their respective geometries. For example, a polyp may be geometrically analogized to a solid ellipsoid and modeled as:

$$M_{Polyp}:(\rho,\theta,\phi) \mapsto x=\rho[a\cos\theta\cos\phi c\sin\theta\cos\phi c\sin\phi]^T \quad (5)$$

where $\rho\in\Pi=[0,1]$, $\theta\in\Theta=[0,2\pi]$, and $\phi\in\Phi=[-\pi/2,\pi/2]$. In this example, the parameters of the model are $m_{Polyp}=(a,c)$. Different choices of $\rho\in\Pi$ define different surfaces at which principal curvatures can be computed, yielding:

$$\rho=(a/c^2)\sqrt{\kappa_2/\kappa_1^3} \text{ and} \quad (6)$$

$$\sin^2\phi=(c^2(\kappa_1/\kappa_2)-a^2)/(c^2-a^2). \quad (7)$$

In this example, the maximum entropy prior on a non-negative random variable with finite mean is the exponential distribution. Thus, where $a \leq c$, the prior $p(m_{Polyp}|M_{Polyp},x)$ where width $I_X(x)=1$ if $x\in X$ and 0 otherwise is given by:

$$p(m_{Polyp}|M_{Polyp},x)=(8/5)\lambda^5 a^2 c e^{-\lambda(a+c)} I_{M_{Polyp}}(m_{Polyp}) \quad (8)$$

where $2/\lambda$ is the expected diameter of a polyp in a given patient cohort.

In this example, a distribution over $x$ can be obtained by sampling from $M_{Polyp}$ according to a Poisson point process. Through a succession of transformations of random variables, $x$ may be mapped to $(\rho,\theta,\phi)$ according to Equation 5 and $(\rho,\theta,\phi)$ may then be mapped to $\kappa$ according to Equations 6 and 7. Using a Laplace-type approximation to solve the integral of Equation 1, an equation defining the probability that a voxel is a polyp may be defined as:

$$p(\kappa|M_{Polyp},x) \approx \frac{1536 \lambda \kappa_2 f_\kappa(f_\kappa(g(\kappa))+3))}{11(3\kappa_1+5\kappa_2)^4} e^{-g(\kappa)} I_{[0,\kappa_2]}(\kappa_1) \quad (9)$$

where $g(\kappa)=\lambda(3\kappa_1+5\kappa_2)/[\kappa_2(3\kappa_1+\kappa_2)]$ and where $f_\kappa(u)=g(\kappa)u\alpha 6$. By solving for Equation 9 based on voxel specific information, a probability that the respective voxel is a polyp as defined by the model may be calculated.

Similarly, an equation defining the probability that a voxel represents a fold in the colon tissue may be geometrically derived, as described above, based on the observation that such folds exhibit a high curvature in one direction, but not in other directions. An example of such an equation is:

$$p(\kappa|M_{Fold},x) = \quad (10)$$

$$\frac{\pi}{4\tau\kappa_2(\kappa_1-\kappa_2)^3} \begin{cases} (-2\kappa_2+\kappa_1(2+\pi(1+\tau\kappa_2)))e^{\frac{1}{\tau\kappa_2}} - \\ (\pi\tau\kappa_1\kappa_2-4(\kappa_1-\kappa_2)I_{(-\infty,0]}(\kappa_1))e^{-\frac{2(\kappa_1-\kappa_2)}{\pi\tau|\kappa_1|\kappa_2}} \end{cases}$$

where $\tau$ is the expected thickness of a colonic fold in a given patient cohort. By solving for Equation 10 based on voxel specific information, a probability that the respective voxel represents a fold in the colon tissue, as defined by the model, may be calculated.

The polyp and colon tissue fold models described above are appearance independent and may be invariant to monotonically increasing image intensity transformations of the CT image data. In particular, such transformations preserve the geometry of isosurfaces in the volume, affecting only the isovalue associated with a given isosurface. Other models however, such as those based on the geometry of the colon wall and/or those which model the noise factor, may be appearance dependent and, thus may vary in response to monotonically increasing image intensity transformations of the CT image data. Such probability models may also be developed making use of geometric assumptions and structural information descriptive of the respective colorectal structure or noise property. For example, in one embodiment the colon wall may be modeled by assuming a simple spherical model of radius R for the colon wall. The probability distribution of the colon wall curvatures, solved as described with respect to the polyp model, may be given by:

$$p(\kappa | M_{Wall}, x) = \qquad\qquad (11)$$
$$(1/(8\sqrt{2\pi}\,\alpha^3))(\kappa_2 - \kappa_1)e^{-\frac{5\kappa_1^2 - 6\kappa_2\kappa_1 + 5\kappa_2^2)R^2 + 4(\kappa_1+\kappa_2)R+4}{32R^2\alpha^2}}$$

where $\alpha = \sigma_n/(2\sigma^2 C)$, $\sigma_n$ is the amplitude of the image noise, $\sigma$ is the scale parameter of a combined point-spread function and image-smoothing kernels, and C is the magnitude of the air-tissue gradient at the colon wall.

In this example, the noise, or outlier, model may be derived based on the probability distribution of the curvature of isosurfaces at arbitrary points in an isotropically correlated Gaussian random field. In this example, the result depends on the dimension n of the Euclidean vector space on which the random field is embdedded and on the second and fourth derivatives of its autocorrelation function $R(\tau)$ at $\tau = 0 \in R^n$. In an example where n=3 and where it is assumed that a good approximation for the image autocorrelation function can be derived from the CT system point-spread function and smoothing kernel, the resulting probability distribution may be described by:

$$p(\kappa | M_{Noise}, x) = \frac{256\sigma^3(\kappa_2 - \kappa_1)}{\pi(4 + 3\sigma^2\kappa_2^2 - 2\sigma^2\kappa_2\kappa_1 + 3\sigma^2\kappa_1^2)^3} I_{(-\infty,\kappa_2]}(\kappa_1), \qquad (12)$$

with $\sigma$ as in Equation 11

The preceding examples of probability models are suitable for use in evaluating voxels adjacent to air within the colon, i.e., voxels at the air interface. As noted above, for voxels adjacent to the contrast-enhanced contents of the colon the gradients are reversed. In particular, for polyps, colon walls, and/or colon folds adjacent to the contrast-enhanced contents, the general shape of the structure is preserved but the gradient directions in the image are inverted. One possible way in which to account for this inversion is, therefore, also invert the curvature values in these regions, since the gradient is normal to the local isosurface, so that the respective probabilities for voxels near the contrast-enhanced contents are:

$$p'(\kappa|M_i,x) = p'(\kappa_1,\kappa_2|M_1,x) = p(-\kappa_2,-\kappa_1|M_i,x) \qquad (13)$$

where p' is the probability density of curvatures given by $M_i$ at voxels x adjacent to contrast-enhanced contents of the colon. Thus, for voxels adjacent to contrast-enhanced contents, the above probability Equations 9, 10, 11, and 12 may be modified to reflect the reversed gradients expected at such voxels.

The probability models for each type of colorectal (or other organ) structure and environment (contrast-enhanced contents interface or air interface) may thus be calculated. In view of these models and environments, a probability may be computed for each voxel on the colon surface for each type of model $M_i$ in view of the voxel environment. In one embodiment, voxels for which the log-likelihood ratio:

$$\log P(M_{Polyp}|x) - \log \Sigma_{i=1} P(M_i|x) \qquad (14)$$

is above a certain threshold are labeled as belonging to a polyp. In one such embodiment, a connected components algorithm may be applied to the labeled data to obtain a set of candidate detections. Such detections may be further thresholded, such as using their average log-likelihood. The result of either threshold step may be swept to generate a fROC curve for review by suitable personnel.

The foregoing example describes one way in which suitable models may be constructed, adapted, and applied, however other embodiments are also possible. In particular, though inverting the signs of curvature at the interface between the tissue and the contrast-enhanced region represents one way in which data at this interface may be handled, other approaches may also be applied. Indeed, in certain embodiments, features other than curvature may be the basis for the modeling process. In particular, any suitable technique that adapts the models (whether based on curvature or otherwise) so that they can handle data in the interface of the tissue and the contrast-enhanced region may be employed. Examples of other suitable techniques include deriving new models using data-driven techniques applied to the data in the interface between the tissue and the contrast-enhanced region.

While the proceeding examples of model derivation generally related to the modeling of colorectal structures, the present techniques may be adapted for modeling other anatomic structures, such as nodules, vessels, and vessel junctions in the lungs. For example, with the foregoing examples in mind, the modeling of other organ structures may be generalized as involving: (i) selecting a suitable geometric representation for $M_i$, (ii) designing the priors $p(m_i|M_i,x)$ and $P(M_i|x)$, (iii) deriving a likelihood $p(\kappa|m_i,M_i,x)$, and (iv) marginalizing $p(\kappa|m_i,M_i,x)$ over $p(m_i|M_i,x)$. In certain embodiments the marginalization steps may be further broken down into simplification of the integrand, such as by employing some variation of Laplace's method, and solving the simplified integral.

The techniques described herein provide various advantages over other classification schemes. For example, voxel labeling as described does not involve image segmentation or classification of segmented regions. Further, voxel labeling as described herein does not utilize an explicit training step. Instead the present techniques benefit from building statistical models from geometric abstractions of the desired label classes (as opposed to empirically modeling the data) and from using available medical data to generate priors for the parameters of the models. In addition, contrary to techniques which employ subtraction techniques to remove contrast-enhanced voxels from the image data, thereby altering the image data being analyzed, the present techniques do not subtract the contrast-enhanced portions of the image from the remainder of the image. Instead, the present techniques leverage the information provided by the contrast-enhanced areas to identify the tissue voxels for further processing and to select the appropriate probabilistic models for use in analyzing the tissue voxels.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method, comprising:
   generating an initial region mask of a volumetric representation of an organ;
   defining a plurality of voxels to be labeled based upon the initial region mask, wherein defining the plurality of voxels to be labeled comprises subtracting an eroded version of the initial region mask from a dilated version of the initial region mask;
   adjusting models used to label the voxels based on neighboring regions of a respective voxel undergoing labeling; and labeling each voxel of the plurality of voxels as corresponding to one of a tissue type, an anatomical structure, or organ contents based using the respective adjusted models.

2. The method of claim 1, wherein the initial region mask comprises voxels corresponding to the interior of the organ.

3. The method of claim 1, wherein the initial region mask comprises voxels corresponding to air within the organ and voxels corresponding to non-tissue contents of the organ.

4. The method of claim 1, wherein the models correspond to geometrically derived models of tissue and/or structures associated with the organ.

5. The method of claim 1, wherein the neighboring region of each voxel comprises a respective cubic region about each respective voxel undergoing labeling.

6. The method of claim 1, wherein the neighboring region of each voxel comprises a region defined by a segmentation algorithm.

7. The method of claim 1, further comprising:
   computing one or more respective features for each tissue voxel of a plurality of tissue voxels;
   calculating a respective gradient for each tissue voxel of the plurality of tissue voxels; and
   labeling each tissue voxel based upon the respective features and the gradient and the proximity of the respective tissue voxel to adjacent structures or contents of an organ.

8. The method of claim 7, wherein the one or more respective feature comprise a curvature.

9. The method of claim 7, wherein each gradient comprise an intensity gradient.

10. The method of claim 7, wherein each gradient comprise a vector pointing from an area of low intensity to an area of high intensity.

11. The method of claim 7, wherein the respective features and/or gradients are used to adapt one or more probabilistic models and each tissue voxel is labeled based upon outputs of the one or more probabilistic models.

12. The method of claim 11, wherein the outputs comprise probabilities that the respective voxels correspond to respective tissue types modeled by each of the probabilistic models.

13. The method of claim 7, wherein labeling each tissue voxel is based at least in part on different geometrical abstractions of different tissue types.

14. The method of claim 7, wherein each tissue voxel is labeled as a type of healthy tissue or as a type of unhealthy tissue.

15. A method, comprising:
   acquiring volumetric image data of an organ using a computed tomography scanner, wherein acquiring the volumetric image data comprises generating an initial region mask of the volumetric image data;
   processing the volumetric image data to identify a plurality of tissue voxels in the volumetric image data, wherein processing the volumetric image data comprises subtracting an eroded version of the initial region mask from a dilated version of the initial region mask; and
   processing the plurality of tissue voxels using two or more models, wherein the proximity of each tissue voxel to different adjacent regions, organ contents or anatomical structures is used to adjust the two or more models.

16. The method of claim 15, wherein each model is derived using geometrical assumptions about a type of tissue being modeled.

17. The method of claim 15, comprising identifying a subset of the plurality of tissue voxels as corresponding to a first tissue type based upon the processing of the plurality of tissue voxels using the two or more models.

18. An image processing system, comprising:
   one or more storage devices storing one or more image processing routines; and
   a processor operationally coupled to the one or more storage devices, wherein the processor is configured to:
      generate an initial region mask of a volumetric representation of an organ;
      define a plurality of voxels to be labeled based upon the initial region mask, wherein defining the plurality of voxels to be labeled comprises subtracting an eroded version of the initial region mask from a dilated version of the initial region mask;
      adjust models used to label the voxels based on neighboring regions of a respective voxel undergoing labeling, and
      label each voxel of the plurality of voxels as corresponding to one of a tissue type, an anatomical structure, or organ contents based upon the respective adjusted models using the one or more image processing routines.

19. The image processing system of claim 18, wherein the one or more storage devices comprise one or more of an optical, magnetic, and/or solid state memory storage structure.

20. A method, comprising:
   generating an initial region mask of a volumetric representation of an organ;
   defining a plurality of voxels to be labeled based upon the initial region mask, wherein defining the plurality of voxels to be labeled comprises subtracting an eroded version of the initial region mask from a dilated version of the initial region mask;
   computing one or more respective features for each tissue voxel of the plurality of tissue voxels;
   calculating a respective gradient for each tissue voxel of the plurality of tissue voxels; and
   labeling each tissue voxel based upon the respective features and the gradient and the proximity of the respective tissue voxel to adjacent structures or contents of the organ.

* * * * *